US000001374H

United States Statutory Invention Registration [19]

[11] Reg. Number: H1374

[43] Published: Nov. 1, 1994

Adam et al.

[54] PARTICLES OF HYDROPHOBIC POLYMERS CONTAINING VOIDS

[75] Inventors: Herve Adam; Henri G. Riess, both of Mulhouse; Claude G. S. Nicaud, Paris, all of France

[73] Assignee: Imperial Chemical Industries plc, Herts, England

[21] Appl. No.: 939,426

[22] Filed: Sep. 4, 1992

Related U.S. Application Data

[63] Continuation of Ser. No. 544,697, Jun. 27, 1990, abandoned.

[30] Foreign Application Priority Data

Jul. 13, 1989 [FR] France ..... 89 4020171

[51] Int. Cl.[5] ..... B32B 3/26; B32B 5/16

[52] U.S. Cl. ..... 428/315.7; 428/402; 428/403; 428/407

[58] Field of Search ..... 428/315.7, 402, 403, 428/407

[56] References Cited

U.S. PATENT DOCUMENTS

| | | | |
|---|---|---|---|
| 3,933,579 | 1/1976 | Kershaw et al. | 162/164.1 |
| 4,064,294 | 12/1977 | Babil et al. | 521/62 |
| 4,385,164 | 5/1983 | Sinclair et al. | 526/201 |
| 4,435,524 | 3/1984 | Dinbergs | 428/402 |
| 4,742,086 | 5/1988 | Masamizu et al. | 521/62 |
| 4,839,395 | 6/1989 | Masamizu et al. | 521/56 |
| 4,863,973 | 9/1989 | Chip et al. | 521/54 |
| 4,920,160 | 4/1990 | Chip et al. | 521/54 |
| 5,045,569 | 9/1991 | Delgado | 428/402 |

FOREIGN PATENT DOCUMENTS

| | | |
|---|---|---|
| 193901 | 2/1984 | Japan . |
| 1288583 | 9/1972 | United Kingdom . |

OTHER PUBLICATIONS

Tioxide Brochure, Formulations with Spindrift, pp. 1–4.

*Primary Examiner*—Philip Tucker

*Attorney, Agent, or Firm*—Cushman, Darby & Cushman

[57] ABSTRACT

Polymer particles each containing at least one void and also a hydrophobic copolymeric surfactant and a hydrophilic copolymeric surfactant. The hydrophobic surfactant comprises long hydrophobic chains anchored in the particles and hydrophilic chains exposed to the voids. The hydrophilic copolymeric surfactant comprises hydrophobic portions anchored in the particles and hydrophilic chains exposed to the surroundings of the particles. The particles have a fine cell structure, are washable to remove unanchored surfactant and are easily dispersible in water. They are useful in coatings, plastics, cosmetics, paper and leather. Also a process for making the particles in which water is dispersed as droplets in monomer containing the hydrophobic surfactant and the dispersion is in turn dispersed in additional water containing the hydrophilic surfactant and the whole is subjected to a polymerisation which forms particles containing voids initially filled with water.

11 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PARTICLES OF HYDROPHOBIC POLYMERS CONTAINING VOIDS

This is a continuation of application Ser. No. 07/544,697, filed on Jun. 27, 1990, which was abandoned upon the filing thereof.

This invention relates a particle of hydrophobic polymer (including copolymer) containing at least one void to a process for making such particles and to their use in products such as coating compositions, plastics, cosmetics, papers or leather.

Particles of hydrophobic polymer containing voids scatter light and so have been used for example in paints as a partial replacement for increasingly expensive opacifying agents or matting agents such as titanium dioxide. British patent GB 1 288 583 describes hydrophobic particles containing a plurality of voids which have been made for example by producing a dispersion of water droplets in hydrophobic monomer (such as styrene) in the presence of low molecular weight surfactants, a free radical polymerisation initiator such as azodiisobutyronitrile and various preformed random copolymers of styrene. This first dispersion (namely water droplets in monomer) is then itself dispersed in a further quantity of water which contains partially hydrolysed polyvinyl acetate to produce a second dispersion in which droplets of the first dispersion are formed in the further quantity of water and stabilised by the polyvinyl acetate. Then this second dispersion is heated to activate the initiator and cause a polymerisation which produces hydrophobic particles each containing a plurality of voids. The voids are usually full of air but may be temporarily or permanently, fully or partially occupied by extraneous material such as minerals, water or even organic liquid provided that the liquid does not harm the hydrophobic polymer. Such particles give opacity and matt appearances to paints but their efficiency is limited by a tendancy for their voids to be large and interconnected and to be exposed (i.e. open) at the surface of the particle as shown for example in FIG. 1 on page 37 of "Progress in Organic Coatings" 10 (1982). The particles also agglomerate if an attempt is made to dry them which means that they cannot easily be supplied as a dry free-flowing powder.

A further disadvantage is that in commercial practice, the particles have to be made using unsaturated polyesters which can lead to problems in achieving reproducibility in manufacture, problems of instability during storage and yellowing of the final product.

An object of this invention is to provide particles of hydrophobic polymer containing at least one void and usually a plurality of voids of better structure and/or such particles which can be washed to remove unanchored surfactant and dried to give a free flowing powder which is re-dispersible in water and/or which has a good compatibility with, for example paint, paper or leather. An object of a refinement of the invention is to provide particles with a more uniform distribution of void sizes and with a reduction and possibly a substantial elimination of voids exposed at the surface of the particle.

Accordingly this invention provides a particle of a hydrophobic polymer containing at least one void and comprising an essentially hydrophobic surfactant in the region of the internal surfaces defining the voids and an essentially hydrophilic surfactant in the region of the external surface of the particle wherein a) the essentially hydrophobic surfactant is a block copolymer having a molecular weight of from 5000 to 150,000 (preferably 10,000 to 40,000) and comprising a hydrophobic chain and at least one (preferably 1 to 3) hydrophilic chains which chain or chains are present in an amount such that the hydrophilic portion of the block copolymer is from 5 to 45% (preferably 10 to 40%) of the weight of the block copolymer and b) the essentially hydrophilic surfactant has a molecular weight of at least 2000 (preferably 3000 to 75,000) and comprises at least one (preferably 1 to 3) hydrophilic chain which chain or chains are present in an amount such that the hydrophilic portion of the essentially hydrophilic surfactant is from 40 to 90% (preferably at least 45% and most usefully 50 to 80%) of the weight of the essentially hydrophilic surfactant.

Copolymers useful in this invention may be made for example according to the general techniques outlined in the article "Block Copolymers" by Riess et al in Volume 2 the "Encyclopedia of Polymer Science and Engineering" edited by H. F. Mark et al and published by John Wiley of New York, see pages 324 to 434 the contents of which are herein incorporated by reference.

The hydrophobic polymer (i.e. the polymer or copolymer which forms the main part of the particle) may be any polymer or copolymer which is not soluble in or swollen by water to an extent which totally destroys any light scattering ability of the voids. Preferably the hydrophobic polymer should be a crosslinked material. Conveniently the hydrophobic polymer should be obtainable by a free radical initiated polymerisation performed on a dispersion of monomer in water in the presence of the surfactants. Suitable monomers include vinyl aromatics such as styrene or divinyl benzene, vinyl acetate, acrylates such as alkyl (especially $C_1$ to $C_6$) esters of acrylic or methacrylic acids and in particular methyl, ethyl or butyl esters or ethylene glycol dimethacrylate, or cyano or halogeno substituted monomers, for example acrylonitrile when copolymerised with styrene. Styrene polymers or copolymers are sometimes preferred because of their high refractive index.

The particles of hydrophobic polymer usually have a number average particle size of from 0.5 to 100 $\mu$m (1 $\mu$m is $10^{-6}$m) and generally it is from 1 to 50 $\mu$m. Refinement of the invention might allow the production of particles as small as 0.3 $\mu$m whereupon the particles will almost certainly each contain only one void. Where the particles are primarily intended for use as opacifying agents, their number average particle size is preferably below 10 $\mu$m.

The essentially hydrophobic surfactant is a block copolymer having a minimum molecular weight (as determined by gel phase chromatography) of 5000 and comprising hydrophobic and hydrophilic chains in an amount such that the hydrophobic portion comprises from 55 to 95 wt % of the copolymer. The high molecular weight and the high proportion of block copolymerised hydrophobic material ensures that the hydrophobic portion of the surfactant anchors firmly into the hydrophobic polymer particle whilst permitting the copolymer to cross a boundary which defines a void so that the hydrophilic chain or chains are exposed to the void and are available for interaction with suitable solids or liquids should any such occupy the void. The essentially hydrophobic surfactant will preferably have an HLB of 1 to 9 (preferably 4 to 8). HLB is described in the third edition of Kirk Othmer's "Encyclopedia of Chemical Technology" Volume 8 published by John Wiley of New York in 1979, see pages 910 to 916, the contents of which are herein incorporated by reference. A preferred essentially hydrophobic surfactant will contain hydrophilic polyoxyethylene chains and for such surfactants, HLB is defined as:

$$\frac{\text{Wt \% Polyoxyethylene in the copolymer}}{5}$$

The preparation of surfactants of this type is discussed more specifically in the article "Preparation de Copolymeres sequences styrolene oxyde d'ethylene" by Finaz et al in "Memoires Presentes a la Societe Chimique" Voulume 164 of 1962 pages 262 to 266 the contents of which are herein incorporated by reference.

Where alternative hydrophilic chains are chosen, it is preferred that the resulting essentially hydrophobic surfactant should have an HLB corresponding to the preferred range of HLB for the surfactants in which the hydrophilic chain is polyoxyethylene. Examples of alternative hydrophilic chains include chains of polymerised oxazoline (non-ionic) or maleic anhydride (ionic) monomers. The preferred hydrophobic chain is a chain of polymerised styrene but alternatives include for example chains of polymerised isoprene, oxypropylene, dimethylsiloxane or alkyl (preferably $C_1$ to $C_6$) esters of acrylic or methacrylic acids.

The essentially hydrophilic surfactant should comprise at least one hydrophilic chain long enough to interact with water or other suitable material in which the particle might be dispersed whilst also comprising a hydrophobic portion which can firmly anchor in the particle. These requirements are achieved if the essentially hydrophilic surfactant has a molecular weight (as determined by gel permeation chromatography) of at least 2000 and the hydrophilic chain or chains amount to 40 to 90wt % of the surfactant. In such circumstances, the essentially hydrophilic surfactant can cross the surface of the particle such that the hydrophobic portion is anchored in the particle whilst the hydrophilic chain or chains are exposed and available for interaction. It is thought that when the particles are dispersed in water, the hydrophilic chains of the essentially hydrophilic surfactant radiate from the surface of the particle like hairs so making the particles more compatible with the water. These "hairy" chains probably also increase the compatibility of the particles with hydrophilic materials such as celluloses, polyvinyl butyrals containing some hydroxyl groups or carboxylic polymers such as polyacrylic or polymethacrylic acids. Where the hydrophilic chain comprises polyethylene oxide or polyoxazoline, then the particles are also usually compatible with alkyl acrylates or methacrylates especially polymethyl methacrylates. It is believed that the chains radiate as far as somewhere between 10 and 20 nm from the surface of the particle depending on the molecular weight of the surfactant.

Preferably the essentially hydrophilic surfactant has an HLB number of from 8 to 18 (most usefully 10 to 16). The preferred chains are polyoxyethylenes but alternatively hydrophilic chains of the types usable in the essentially hydrophobic surfactant may be chosen provided they confer a similar HLB. Likewise the preferred hydrophobic portion comprises a polystyrene chain but chains of the types used in the essentially hydrophobic surfactant may be chosen.

The voids can have number average (Dn) diameters of from 0.1 μm upwards to say 10 μm and volume average diameters (Dv) of from 0.2 μm to say 20 μm although in practice the ranges are usually 0.1 to 5 μm (Dn) and 0.2 to 10 μm (Dv). The particles may optionally contain various additives and in particular particulate minerals such as titanium dioxide which improve opacity.

This invention also provides a process for making hydrophobic particles comprising at least one void by dispersing droplets of water (optionally containing other material) in a hydrophobic monomer immiscible with water and dispersing the dispersion in a further quantity of water (also optionally containing other materials and causing the monomer to polymerise wherein a) the monomer contains an essentially hydrophobic surfactant as hereinbefore defined and
b) the further quantity of water contains an essentially hydrophilic surfactant as hereinbefore defined.

Polymerisation produces particles according to this invention comprising voids initially occupied by water. The water may be retained or removed by diffusion through the particle and subsequent evaporation from the surface of the particle. If the droplets of water initially contain a dispersion of particles or an involatile solute, then a residue of these materials will be left in the voids or possibly even in the hydrophobic polymer which forms the main part of the particle. Otherwise a void will usually contain air.

The dispersions used in this invention can be made by conventional techniques such as stirring or ultrasonic vibration. Preferably the monomer phase contains from 0.5 to 15 wt % (based on the monomer) of essentially hydrophobic surfactant whilst the further quantity of water preferably contains from, 0.1 to 10 wt % (especially 0.5 to 5 wt %) based on the water phase of essentially hydrophilic surfactant. The presence of the predominantly hydrophobic surfactnnt increases the stability of the water and monomer system leading to improved control of void size. Sometimes, this effect can be enhanced by the inclusion of a thickening agent in the first (water in monomer) dispersion. Suitable thickening agents may be preformed polymers (including copolymers) which are soluble or swellable by monomer, for example a preformed polystyrene.

The system can often be further stabilised by the inclusion of a thickening agent in the further amount of water (i.e. the water in which the first dispersion is dispersed) where a suitable thickener would be a high molecular weight (20,000 to 400,000) polyoxyethylene.

Polymerisation of the monomer may be conveniently achieved by adding a free radical initiator to the monomer phase. Suitable initiators include azodi-isobutyronitrile or peroxides such as lauroyl peroxide, benzoyl peroxide or most preferably an initiator which does not evolve a gas, for example cyclohexyl percarbonate. Polymerisation can be easily initiated by heating the system to a temperature at which the free radical initiator decomposes, generally 30√ to 80° C. Preferably the system should not be stirred during polymerisation but instead left static.

It has been discovered that smaller and more uniform voids can be obtained if lesser amounts of water are dispersed in the monomer and if the droplets of water so dispersed contain a solute which increases osmotic pressure. The solute may be an electrolyte or a substance which is miscible with water but which does not swell the hydrophic polymer. Preferably when such a solute is used, the dispersion of water droplets in monomer should comprise from 5 to 40 wt % of water. Preferably the droplets contain from 0.01 to 1.0 molar solution of formic acid or an amount of an alternative electrolyte which causes a similar increase in osmotic pressure. Alternative electrolytes include hydrochloric acid, phosphoric acid, sodium chloride and ethylene glycol. Use of increased osmotic pressure leads to voids having a Dn of from as little as 0.1 to 0.3 and Dv of as little as 0.2 to 0.6 μm and the substantial elimination of voids exposed at the surface of the particle.

This invention further provides a coating composition, plastics composition, cosmetic, paper or leather containing particles according to the invention or made by the process of this invention.

The invention is further illustrated by the following Examples.

EXAMPLES 1 and 2

Hydrophobic Particles comprising Polyethylene oxide Surfactants

The following mixtures were made:

TABLE 1

| Ingredients | Parts by Weight Example 1 | Example 2 |
|---|---|---|
| Styrene monomer | 45.0 | 32.5 |
| Divinyl benzene monomer | — | 10.0 |
| Essentially hydrophobic triblock copolymer of *PEO-PS-PEO of molecular weight 25,000 containing 30 wt % PEO and 70 wt % PS of HLB 6. | 2.5 | 2.5 |
| Polystyrene | — | 2.5 |
| Cyclohexyl percarbonate | 2.5 | 2.5 |

*PEO is Polyethylene oxide
PS is Polystyrene chain 50 parts by weight of water were added to each of the above mixtures which were then stirred at high speed (about 8000 rpm) until a dispersion of water droplets in monomer was obtained. This dispersion was then in turn dispersed in a further 100 parts by weight of water using high speed (8000 rpm) stirring. The further water contained 1 wt % of an essentially hydrophilic surfactant which was a triblock copolymer of PEO-PS-PEO having a molecular weight of 11000 and comprising 73 wt % PEO and 27 wt % PS giving an HLB of 15. A white mulsion of the first dispersion in the further water was obtained.

The emulsions were each in turn heated to 60° C. in a closed pressure vessel and the temperature was maintained at 60° C. for 12 hours. Dispersions of particles of either polystyrene (Example 1) or styrene/divinyl benzene crosslinked copolymer were obtained and each particle contained a plurality of voids. The dispersions were passed through a 50 μm sieve and concentrated by centrifugation. The particles had the following characteristics:

TABLE 2

| Example | Dv μm Particle | Dv μm Void | Dn μm Void | % Volume of Voids |
|---|---|---|---|---|
| 1 | 6.2 | 5.2 | 2.5 | 45 |
| 2 | 16 | 4.1 | 1.6 | 45 |

The particles could be washed to remove unanchored surfactant and dried to produce a powder which could be easily re-dispersed in water. They were compatible with a wide range of materials.

EXAMPLES 3 and 4

Improving Void Structure

Two amounts of the following mixture were made:

| Ingredient | Parts by weight |
|---|---|
| Styrene monomer | 75 |
| Divinyl benzene monomer | 10 |
| Essentially hydrophobic PS-PEO diblock copolymer of molecular weight 24,000 containing 67 wt % PEO and 33 wt % PS and of HLB 13.4. | 10 |
| Cyclohexyl percarbonate | 5 |

To each of the above mixtures were added 20 parts by weight of water containing a 0.1 molar solution of an acid. The acids were:

| | |
|---|---|
| Example 3 | hydrochloric acid |
| Example 4 | formic acid |

The mixtures were subjected to high speed (8000 rpm) stirring for a sufficient period of time (about five minutes) to produce a dispersion of droplets of acidified water in monomer. This dispersion was then in turn dispersed ultrasonically in a further 300 parts by weight of water which contained 1 wt % of the essentially hydrophilic triblock copolymer used in Examples 1 and 2 and which also contained 3 wt % of a polyethylene oxide thickening agent of molecular weight 400,000. An emulsion was obtained which was caused to copolymerise using the procedure of Example 2.

Particles of copolymer each containing a plurality of voids, were obtained which had a much finer structure as shown in Table 3.

TABLE 3

| Example | Dv μm Particle | Dv μm Void | Dn μm Void | % Volume of Voids |
|---|---|---|---|---|
| 3 | 7 | 1 | 0.3 | 55 |
| 4 | 4.5 | 0.6 | 0.3 | 30 |

Moreover, few if any of the voids were exposed at the surface of the particles. As before, the particles could be washed to remove unanchored surfactant, dried and subsequently re-dispersed in water.

EXAMPLES 5 and 6

Alternative Hydrophobic Polymers

The following mixtures were made:

TABLE 4

| Ingredients | Parts by Weight Example 5 | Example 6 |
|---|---|---|
| Styrene monomer | 55 | — |
| Divinyl benzene monomer | 10 | 10 |
| Acrylonitrile monomer | 20 | — |
| Methyl methacrylate monomer | — | 75 |
| Essentially hydrophobic PEO-PS diblock copolymer of molecular weight 24,000 containing 33 wt % PEO and 67 wt % PS and of HLB 6.7. | 10 | 10 |
| Cyclohexyl percarbonate | 5 | 5 |

20 parts by weight of water containing a 0.1 molar concentration of hydrochloric acid was added to each of the above mixtures and subjected to high speed stirring (8000 rpm for about 5 minutes) to produce two dispersions of acidified droplets of water in monomer. These dispersions were then in turn dispersed ultrasonically in a further 300 parts by weight of water which contained 1 wt % of the essentially hydrophilic surfactant used in Examples 1 and 2. Emulsions were obtained which were caused to copolymerise using the technique of Example 2 except that the emulsions were heated to 50° C. instead of 60° C.

Particles of crosslinked styrene/divinyl benzene/acrylonitrile copolymer or of polymethyl methacrylate were obtained each containing a plurality of finely structured voids as shown in Table 5. Few, if any of the voids were exposed at the surface of the particles and as before the particles could be washed to remove unanchored surfactant, then dried and subsequently re-dispersed in water.

TABLE 5

| Example | Dv μm Particle | Dv μm Void | Dn μm Void | % Volume of Voids |
|---|---|---|---|---|
| 5 | 17 | 4.3 | 3.1 | 45 |
| 6 | 17 | 5.2 | 3.0 | 65 |

EXAMPLE 7

Alternative Hydrophobic Surfactant

The following mixture made:

| Ingredient | Parts by Weight |
|---|---|
| Styrene | 88 |
| Divinyl benzene | 2 |
| Essentially hydrophobic triblock copolymer of *PEO-PIS-PEO of molecular weight 33000 containing 35 wt % PEO and 65 wt % PIS of HLB 7 | 5 |
| Cyclohexyl percarbonate | 5 |

*PIS is polyisoprene 100 parts by weight of water was added to the above mixture and subjected to ultrasonic vibration for about 5 minutes to produce a dispersion of droplets of water in monomer. This dispersion was then in turn ultrasonically dispersed in 300 parts of water containing 1 wt % of the essentially hydrophilic surfactant used in Examples 1 and 2 and 3 wt % of a polyethylene oxide thickener of molecular weight 400 000. An emulsion was obtained which was caused to copolymerise using the technique of Example 2.

Particles of a crosslinked stryene/divinyl benzene copolymer were obtained each containing a plurality of voids having dimensions as shown below:

TABLE 6

| Dv μm Particle | Dv μm Void | Dn μm Void | % Volume of Voids |
|---|---|---|---|
| 6.5 | *4 | *2 | 20 |

*Expected values but not measured.

What we claim is:

1. A particle of a hydrophobic polymer containing at least one void and comprising an essentially hydrophobic surfactant in the region of the internal surfaces defining the voids and an essentially hydrophilic surfactant in the region of the external surface of the particle wherein a) the essentially hydrophobic surfactant is a block copolymer having a molecular weight of from 5,000 to 150,000 and comprising a hydrophobic chain and at least one hydrophilic chain which chain is present in an amount such that the hydrophilic portion of the block copolymer is from 5 to 45% of the weight of the block copolymer and b) the essentially hydrophilic surfactant has a molecular weight of at least 2,000 and comprises at least one hydrophilic chain which chain is present in an amount such that the hydrophilic portion of the essentially hydrophilic surfactant is from 40 to 90 of the weight of the essentially hydrophilic surfactant, whereby the particle when dry is free-flowing in the presence of like particles and can be dispersed in water.

2. A particle according to claim 1 wherein the essentially hydrophobic surfactant has a molecular weight of from 10,000 to 40,000.

3. A particle according to claim 1 wherein the essentially hydrophobic surfactant comprises from 10 to 40 wt % of hydrophilic chains.

4. A particle according to claim 1 wherein the essentially hydrophobic surfactant comprises from 1 to 2 hydrophilic chains.

5. A particle according to claim 1 wherein the essentially hydrophilic surfactant has a molecular weight of from 3000 to 75,000.

6. A particle according to claim 1 wherein the essentially hydrophilic surfactant comprises from 50 to 80 wt % of hydrophilic chains.

7. A particle according to claim 1 wherein the essentially hydrophilic surfactant comprises from 1 to 3 hydrophilic chains.

8. Particles according to claim 1 wherein the number average particle size of the particles is from 0.3 to 100 μm.

9. Particles according to claim 8 wherein the number average particle size of the particles is from 0.5 to 50 μm.

10. Particles according to claim 8 having a number average particle size of below 10 μm.

11. Particles according to claim 8 containing voids wherein the number average diameter of the voids is from 0.1 to 10 μm.

* * * * *